United States Patent
Dragan et al.

[11] Patent Number: 6,135,771
[45] Date of Patent: Oct. 24, 2000

[54] DENTAL CARTRIDGE HAVING AN ATTACHABLE DELIVERY PORTION

[75] Inventors: William B. Dragan, Easton; Gordon Rowe, Wallingford, both of Conn.

[73] Assignee: Centrix, Inc., Shelton, Conn.

[21] Appl. No.: 08/982,951

[22] Filed: Dec. 2, 1997

[51] Int. Cl.[7] .............................. A61C 5/04; A61M 5/24
[52] U.S. Cl. ............................................ 433/90; 604/201
[58] Field of Search ........................ 433/89, 90; 604/200, 604/201, 206, 241

[56] References Cited

U.S. PATENT DOCUMENTS

| | | | |
|---|---|---|---|
| 1,819,258 | 8/1931 | Nevin | 604/200 |
| 2,232,978 | 2/1941 | Smith . | |
| 2,668,534 | 2/1954 | Barradas et al. . | |
| 2,828,743 | 4/1958 | Ashkenaz et al. | 604/201 |
| 3,480,014 | 11/1969 | Callahan | 604/201 |
| 4,430,081 | 2/1984 | Timmermans . | |
| 4,648,532 | 3/1987 | Green | 604/200 |
| 4,752,288 | 6/1988 | Hussey | 604/200 |
| 4,758,158 | 7/1988 | Pierce et al. | 433/90 |
| 4,768,954 | 9/1988 | Dragan | 433/90 |
| 4,973,248 | 11/1990 | Sigler | 433/90 |
| 5,026,283 | 6/1991 | Osanai et al. | 433/90 |
| 5,100,320 | 3/1992 | Martin et al. | 433/90 |
| 5,172,807 | 12/1992 | Dragan et al. | 433/90 |
| 5,289,919 | 3/1994 | Fischer . | |
| 5,306,147 | 4/1994 | Dragon et al. . | |
| 5,409,125 | 4/1995 | Kimber et al. | 604/241 |
| 5,779,668 | 7/1998 | Grabenkort . | |
| 5,836,922 | 11/1998 | Hansen et al. | 604/200 |
| 5,871,355 | 2/1999 | Dragan et al. | 433/90 |

*Primary Examiner*—Ralph A. Lewis
*Attorney, Agent, or Firm*—Fattibene & Fattibene; Arthur T. Fattibene; Paul A. Fattibene

[57] ABSTRACT

A dental cartridge or capsule for dispensing a dental material, such as an amalgam, cement, or glass ionomer. A body portion has a reduced diameter end. A frangible seal is placed adjacent or within the reduced diameter end. A delivery portion or cap has a metal cannula extending there through. The delivery portion or cap is snap fit onto the reduced diameter end. The metal cannula is positioned within the delivery portion or cap so as to rupture the frangible seal in the reduced diameter end of the body portion when the delivery portion or cap is snap fit onto the reduced diameter end. A material placed within the body portion of the dental cartridge is sealed within the body portion, and prevented from entering and thereby possibly clogging the delivery portion of the dental cartridge having a relatively small diameter bore or lumen prior to placement of the delivery portion or cap. In another embodiment the frangible seal is formed by a twist-off tab at the end of the reduced diameter portion. The mixing of a first component, typically a powder, and a liquid component of a dental material is greatly facilitated.

15 Claims, 6 Drawing Sheets

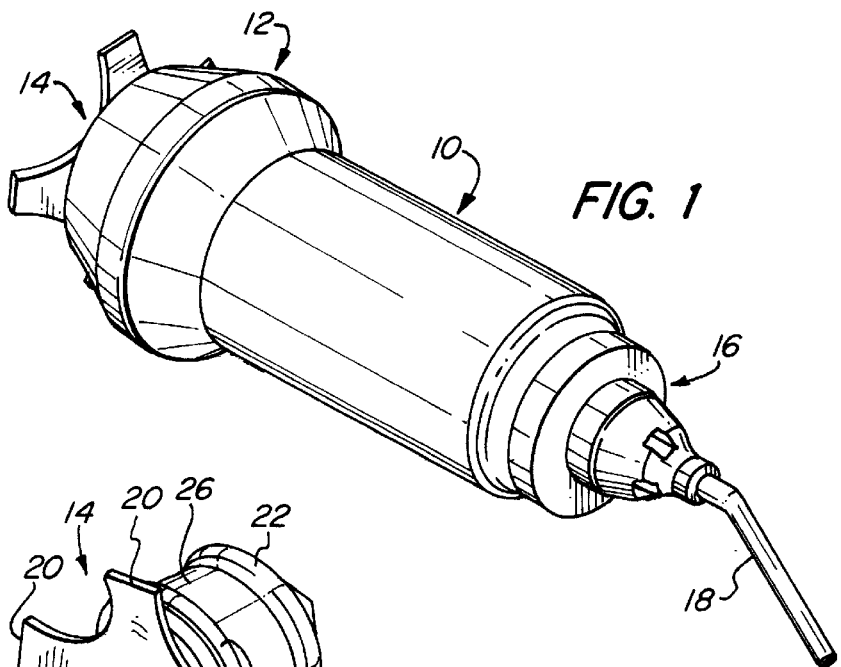
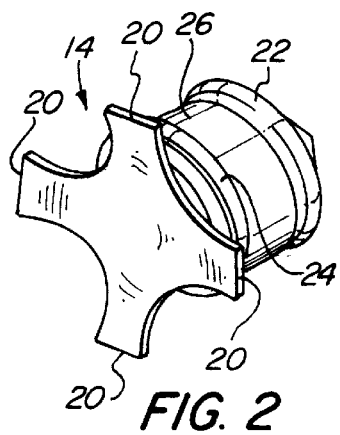
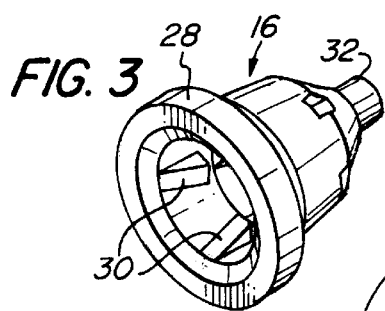
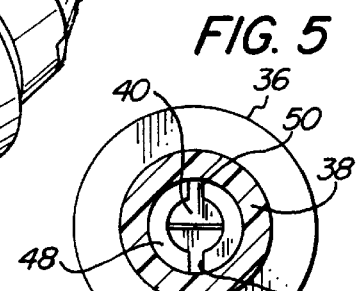
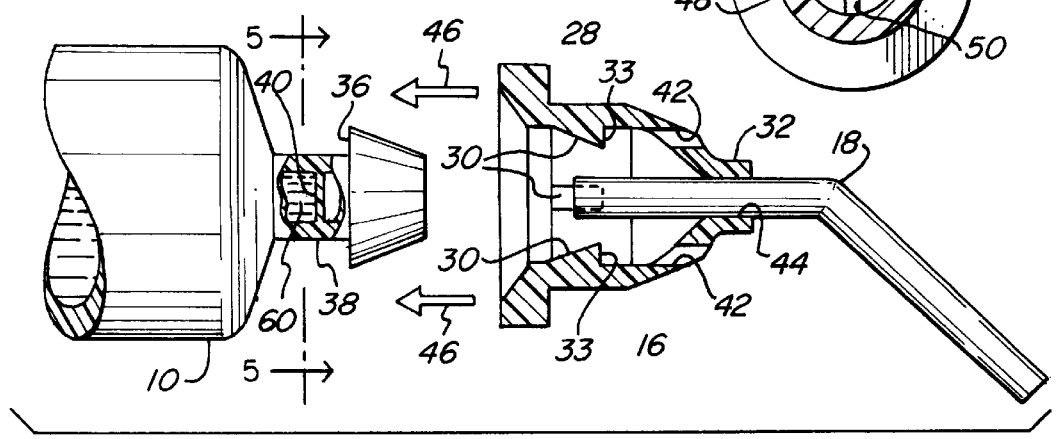

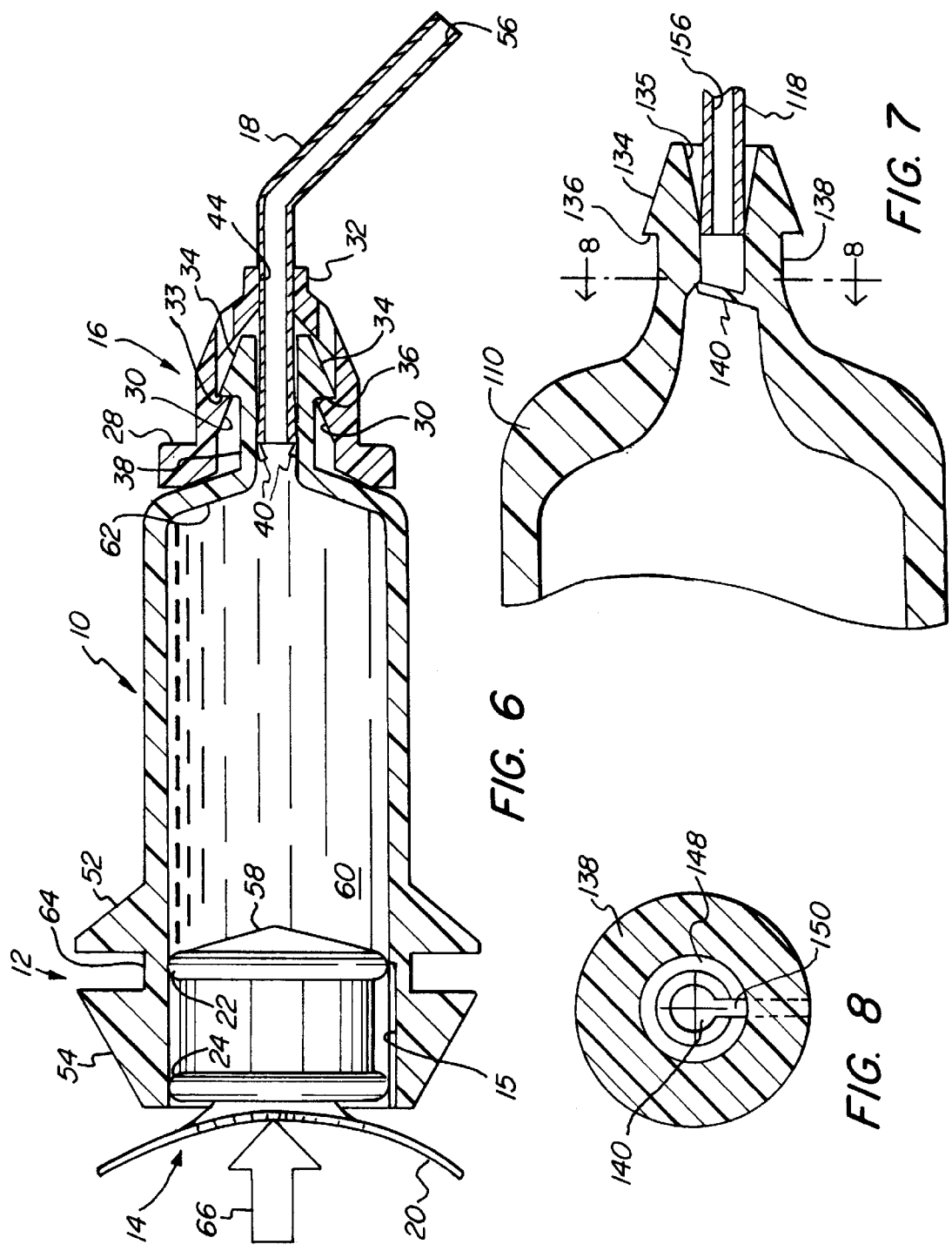

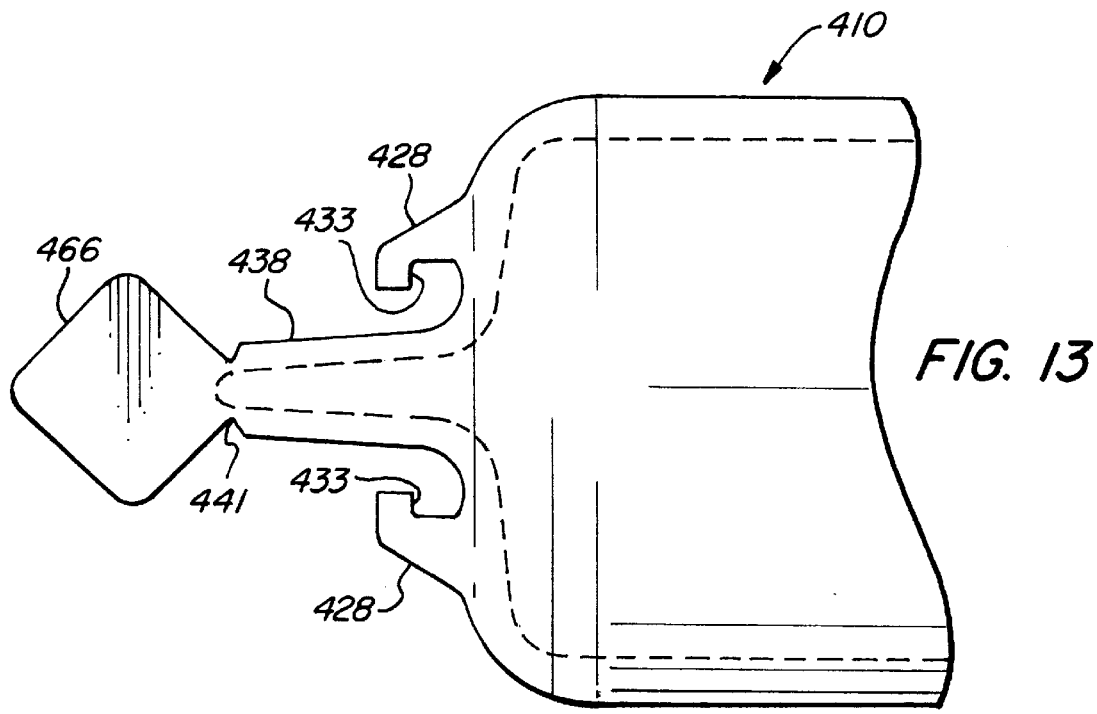
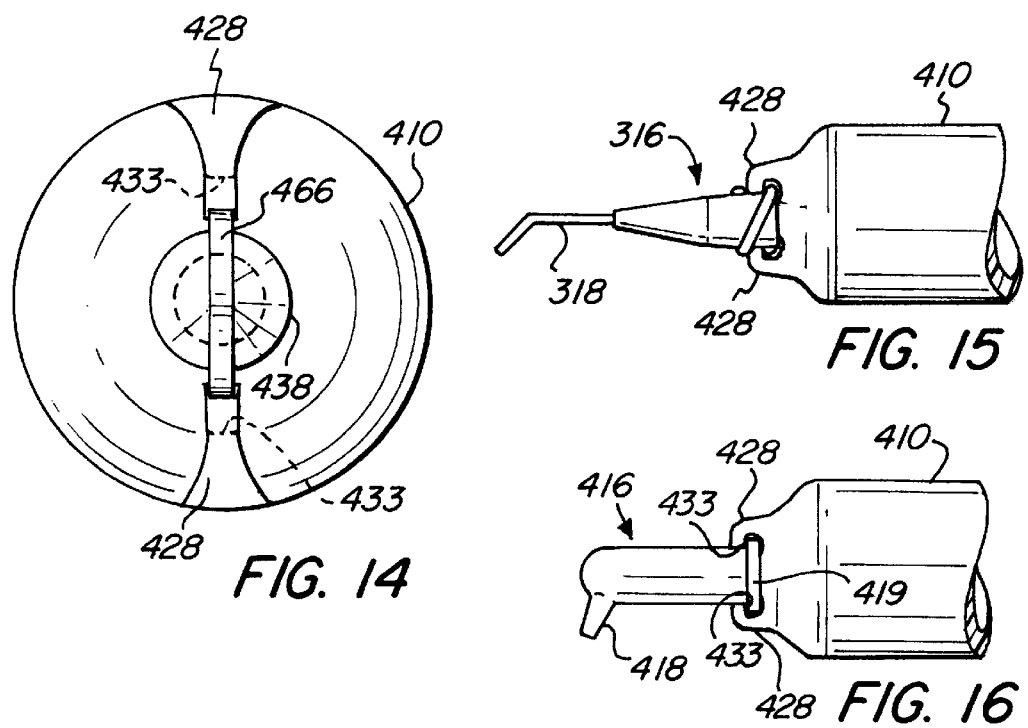

DENTAL CARTRIDGE HAVING AN ATTACHABLE DELIVERY PORTION

FIELD OF THE INVENTION

The present invention relates generally to a dental cartridge used to deliver dental material, and particularly to a cartridge having a delivery portion with a cannula that attaches to the front of the cartridge.

BACKGROUND OF THE INVENTION

In dentistry, it is common to dispense different dental materials with a cartridge used in combination with a syringe. In many applications, the dental material is required to be mixed within the cartridge, such as in the use of amalgam, cement, or glass ionomer materials. Some dental capsules may come prepackaged or premixed. Additionally, some capsules are not able to be dispensed from the capsule directly. Many prepackaged capsules are limited in the volume of material that can be mixed because of the limited amount of component materials that are prepackaged, such as a volume of liquid. A first component of a material is usually placed within a cartridge or capsule and mixed with a liquid component in a mechanical mixer, such as an amalgamator, prior to dispensing. While mixing these dental materials, it is required to keep the first component, which is typically a powder, from entering the delivery portion of the cartridge or capsule. The delivery portion is usually a reduced diameter cannula having a lumen or small bore therein. Problems often occur in that an unmixed portion of the first component will inadvertently enter the lumen and cause blockage. This prevents dispensing of the mixed dental material contained within the body of the cartridge. Material and time is often wasted in that the defective cartridge must be thrown away, and the process of mixing the dental material started over. This is inconvenient in that the patient must typically wait, after being prepared for application of the dental material, until the dentist can prepare another cartridge of dental material. Additionally, the dentist looses valuable productive time. Various methods have been used in an attempt to prevent unintentional blockage of the lumen with dental material before being mixed. Such solutions have been in the form of pins inserted within the lumen to prevent material unintentionally entering the lumen, and seals placed between the lumen and the interior body portion of a cartridge. However, these methods are often inconvenient to use and not completely reliable. One such cartridge is disclosed in U.S. Pat. No. 5,172,807 entitled "Cement Mixing Capsule" and issuing to Dragan et al on Dec. 22, 1992, which is herein incorporated by reference. Therein disclosed is a dental cartridge or capsule having a frangible seal placed between a nozzle and the body portion of the capsule to prevent unmixed cement from entering the nozzle. Another cartridge and dental syringe is disclosed in U.S. Pat. No. 5,306,147 entitled "Dental Syringe and Cartridge Therefor" issuing to Dragan et al on Apr. 26, 1994, which is herein incorporated by reference. While these prior devices and methods have proven useful, there is a need for a more reliable and easily manufactured dental cartridge for use with dental materials requiring mixing or requiring to be temporally separated from a cannula used for dispensing or applying the dental material.

SUMMARY OF THE INVENTION

The present invention is a dental cartridge for dispensing a dental material with a delivery portion having a cannula that snaps onto a reduced diameter end of the cartridge. A frangible seal is placed adjacent or within the reduced diameter end of the cartridge separating the reduced diameter end from the larger body portion of the cartridge. A delivery portion or cap having a cannula fixed therein snaps onto the reduced diameter portion. The cannula extends sufficiently far to enter the reduced diameter portion of the cartridge and puncture the frangible seal therein. In another embodiment a twist-off tab is used as a frangible seal. In one embodiment, the delivery portion or cap is securely held onto the reduced diameter end of the cartridge by a snap fit locking mechanism. Flow between the body portion of the cartridge and the cannula in the delivery portion or cap is thereby securely established. A plug having flexible ears or handles thereon is inserted into the back end of the cartridge to force the material out of the cartridge and through the lumen of the cannula for application of the mixed dental material to the patient. The plug may be advanced by any convenient dispensing device, such as a syringe or other mechanical applicator.

Accordingly, it is an object of the present invention to provide a cartridge with a seal that will break or rupture only when intended.

It is a further object of the present invention to permit mixing of a dental material without unintentionally blocking or clogging the delivery end of the cartridge or cannula.

It is an advantage of the present invention that a metal cannula may be used permitting bending to facilitate placement of the dental material.

It is a further advantage of the present invention that the dentist may select different sized cannulas to be used in combination with a single dental cartridge.

It is a feature of the present invention that the dispensing cannula is used to break a frangible seal.

It is another feature of the present invention that a twist-off tab provides a frangible seal.

It is a further feature of the present invention that the plug or piston used with the cartridge has flexible ears for grasping.

It is a further feature of an embodiment of the present invention that the delivery portion or cap snaps onto a reduced diameter end of the cartridge body.

These and other objects, advantages, and features will become readily apparent in view of the following more detailed description.

BRIEF DESCRIPTION OF THE DRAWINGS

FIG. 1 is a perspective view of an embodiment of the present invention.

FIG. 2 is a perspective view of a plug.

FIG. 3 is a perspective view of a delivery portion or cap.

FIG. 4 is a partial cross section and exploded view of a front portion of the present invention.

FIG. 5 is a cross section taken along line 5—5 in FIG. 4.

FIG. 6 is a longitudinal cross section of an embodiment of the present invention.

FIG. 7 is a cross section of a portion of an embodiment of the present invention.

FIG. 8 is a cross section taken along line 8—8 in FIG. 7.

FIG. 13 is a partial side view illustrating the front portion of another embodiment of the present invention.

FIG. 14 is a front view of the embodiment illustrated in FIG. 13.

FIG. 15 is a partial side view illustrating the front portion of the embodiment illustrated in FIGS. 13 and 14 adapted to receive a threaded delivery portion.

FIG. 16 is a partial side view illustrating the front portion of the embodiment illustrated in FIGS. 13 and 14 adapted to receive a delivery portion having a flange.

DETAILED DESCRIPTION OF THE PREFERRED EMBODIMENTS

Figure 9:
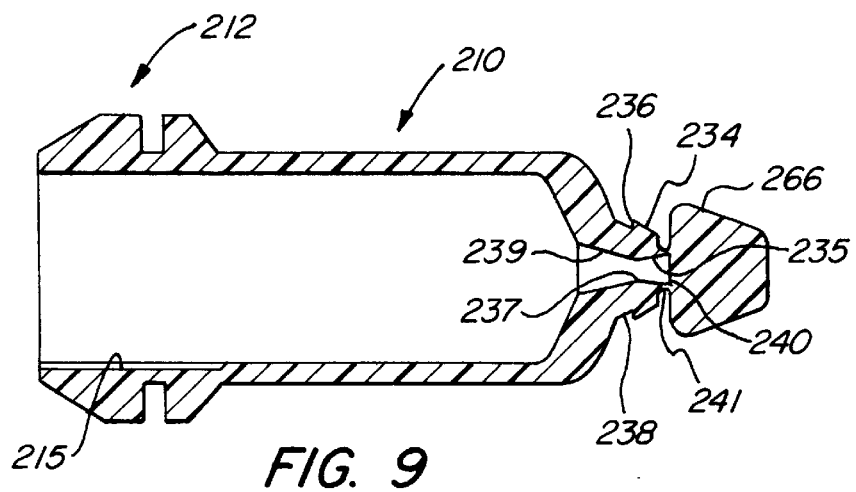
FIG. 9 schematically illustrates another embodiment of the present invention without a delivery portion placed thereon.

FIG. 1 generally illustrates an embodiment of the present invention. A dental cartridge is comprised of a body 10 having a holding or collar end portion 12 and a delivery portion, cap or nozzle means 16. The dental cartridge may be made of any suitable material, for example plastic. Held within delivery portion, cap or nozzle means 16 is tube or cannula 18. The cannula 18 may be held with friction or sealed or glued in place. Sealing the larger diameter open end of body 10 is a piston or plug 14. Typically, material is placed within the body 10 of the cartridge and mixed prior to placement of the delivery portion, cap or nozzle means 16 on the other end of the body 10. The material, which is preferably dental material, is then dispensed through the cannula 18. The cannula 18 is preferably made from metal that is easily bent, but may be made from any marterial.

FIG. 2 more clearly illustrates the piston or plug 14 illustrated in FIG. 1. The piston or plug 14 is comprised of a generally cylindrical body having handles or ears 20 formed on one end. The handles or ears 20 are flexible and facilitate grasping or holding of the plug 14 for insertion and removal permitting easy filling of the cartridge with material. The handles or ears 20 extend radially beyond the generally cylindrical body of the plug 14. Additionally, the ears 20, being flexible, bend backwards and do not interfere with the advancing motion of the plug 14 when pushed through the body 10 of the cartridge by a syringe or other mechanical applicator, not shown. The plug 14 also has a front wipe 22 and a rear wipe 24 with an intermediate portion 26 therebetween.

FIG. 3 more clearly illustrates the delivery portion or cap 16 illustrated in FIG. 1. However, FIG. 3 illustrates the delivery portion or cap without the cannula 18 inserted. The interior space of delivery portion or cap 16 has a plurality of ramps 30 equidistantly spaced therein. A flange 28 provides a grasping area to facilitate pushing the delivery portion or cap 16 onto the cartridge body 10. The reduced cap portion 32 is sized to retain the cannula 18, shown in FIG. 1.

FIG. 4 more clearly illustrates the front end portion of the cartridge. The cartridge body 10 has a reduced neck or diameter portion 38 with a locking means formed thereon. The locking means may have any structure capable of locking or firmly holding on to a delivery portion or cap 16. By way of example, the locking means comprises an angled surface 34 and an exterior shoulder or bearing surface 36. The delivery portion or cap 16 has latching ramps 30 therein that have an interior shoulder or bearing surface 33 that is adapted to mate with exterior shoulder 36. Preferably, there are four ramps 30 equally spaced around the inside diameter of the delivery portion or cap 16. Cap or delivery portion 16 has a flange 28 thereon. The flange 28 facilitates holding of the delivery portion or cap 16 and placement onto the cartridge body 10. One end of the cap 16 has a reduced diameter cap portion 32. The reduced diameter cap portion 32 has a bore 44 therein. The bore 44 is sized to frictionally receive and hold securely the cannula 18. Cannula 18 may be made of any material, but is preferably made of a bendable metal material, such as a soft stainless steel. Openings or vents 42 are placed within the delivery portion or cap 16 and help to prevent entrapping air upon placement of the cap 16 onto the cartridge body 10. Additionally, openings 42 are helpful in the molding process. A frangible diaphragm 40 seals the opening within the reduced portion 38. The frangible diaphragm 40 prevents dental material 60 from being dispensed from the cartridge until the frangible diaphragm 40 is ruptured. After preparation or mixing of the dental material 60 contained within the body 10 of the cartridge, the delivery portion or cap 16 is moved in the direction of arrows 46 to become locked with a snap fit onto the end of the body 10. The ramps 30 are caused to slide over the angled surface 34 and when fully positioned, the internal shoulder 33 mates with the external shoulder 36, securely holding the delivery portion or cap 16 onto the reduced diameter portion 38 of the body 10. A portion of the cannula 18 extends within the interior of the delivery portion or cap 16 sufficiently far so as to strike the frangible diaphragm 40, causing it to rupture. The end of the cannula 18 then extends into the body 10 of the cartridge, permitting the prepared dental material 60 to flow therein. Angled surface 34 seals the opening 42.

FIG. 5 is a cross section taken along line 5—5 in FIG. 4. FIG. 5 more clearly illustrates an embodiment of the diaphragm 40. Diaphragm 40 comprises a thin wall or seal which effectively prevents dental material from escaping or traveling out of the cartridge body. Scored or reduced thickness sections 48 help to provide a weakened portion for more easily rupturing the frangible diaphragm 40 with the cannula. The scored or reduced thickness sections 48 circumscribe the frangible diaphragm 40, with the diaphragm 40 comprised of two sections. Each section is attached to the reduced diameter portion 38 by a hinge 50. The hinges 50 prevent the frangible diaphragm 40 from breaking free and mixing with the dental material contained within the body of the cartridge. While this embodiment is illustrated with two sections, clearly any number of sections may be provided.

FIG. 6 illustrates an embodiment of the present invention in assembled form. The end portion or holding collar 12 has a front shoulder 52 and a rear shoulder 54 forming a groove or channel 64. Typically, a holding device is placed within the groove channel 64 to hold the cartridge body 10 in position while a plunger, not shown, is advanced to contact the back of the plug or piston 14. For example, the cartridge body 10 may be placed in a syringe or applicator device such as that disclosed in U.S. Pat. No. 5,306,147 entitled "Dental Syringe and Cartridge Therefor", which is herein incorporated by reference. The plug or piston 14 is advanced in the direction of arrow 66 so as to extrude the material 60 contained within the body 10 of the cartridge. A vent 15 is placed in a portion of the body 10 so that air is permitted to escape as the plug or piston 14 is advanced into the body 10. Alternately, the vent may be molded into the plug or piston 14. The delivery portion or cap 16 being snapped into position on the front reduced diameter portion 38 of the body 10 is securely held in position by the mating shoulders 33 and 36 of the ramps 30 and angled surface 34. The end of the cannula 18, placed within the delivery portion or cap 16 has a sufficient length to break or pierce the frangible diaphragm 40. Accordingly, by placement of the delivery portion or cap 16 on the reduced diameter portion 38 of the cartridge body 10, the breaking or rupturing of the frangible diaphragm 40 is assured. As the plug or piston 14 is advanced, dental material 60 is extruded through the bore or lumen 56 of the cannula 18, to be delivered, typically into a patient's prepared tooth. The front surface 58 of the plug 14 may be formed to compliment the front body surface 62. In this way, nearly all of the dental material 60 contained within the cartridge is extruded, resulting in very little waste.

FIG. 7 illustrates another embodiment of the present invention. In FIG. 7, only a portion of the body 110 is illustrated for convenience. The reduced diameter portion 138 has a frangible diaphragm or seal 140 therein. The front portion of the reduced diameter portion 138 has an exterior angled surface 134 and an interior angled surface 135. The interior angled surface 135 facilitates and guides the placement of the cannula 118. Cannula 118 also has a bore or lumen 156. A shoulder 136 is formed at one end of the exterior angled surface 134. A complimentary mating shoulder is formed on a delivery portion or cap similar to that illustrated in the previous figures, however, for convenience this is not illustrated in FIG. 7.

FIG. 8 more clearly illustrates the frangible diaphragm or seal 140, illustrated in FIG. 7. FIG. 8 is a cross section taken along lines 8—8 in FIG. 7. In this embodiment, the frangible diaphragm or seal 140 is formed by a scored or reduced thickness portion 148 circumscribing a substantial portion of the frangible diaphragm 140. A land or hinge 150 is used to secure the frangible diaphragm 140 to the reduced diameter portion 138 when the scored or reduced thickness section 148 is ruptured or broken by the cannula 118, illustrated in FIG. 7.

Figure 10:
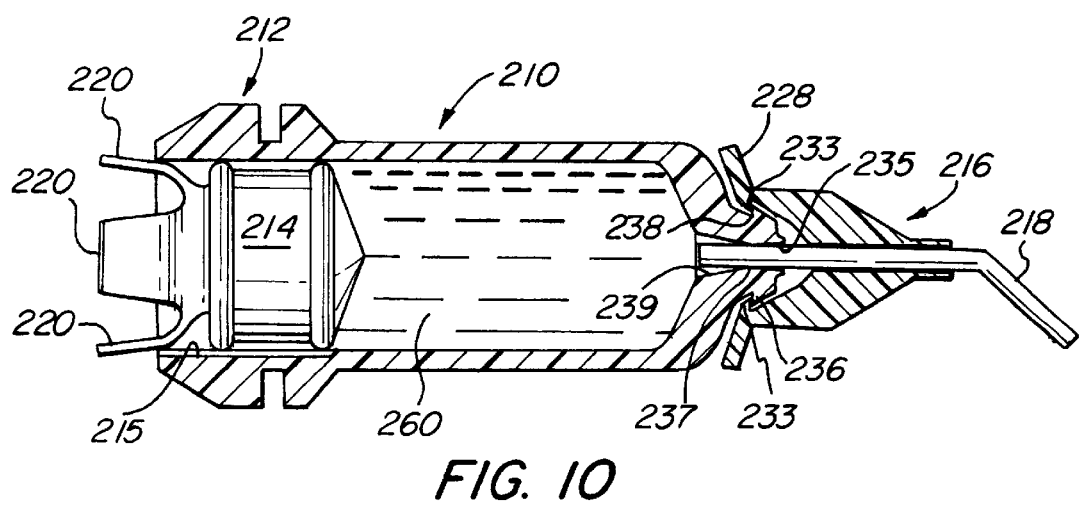
FIG. 10 schematically illustrates the embodiment illustrated in FIG. 9 with a delivery portion placed thereon.
Figure 11:
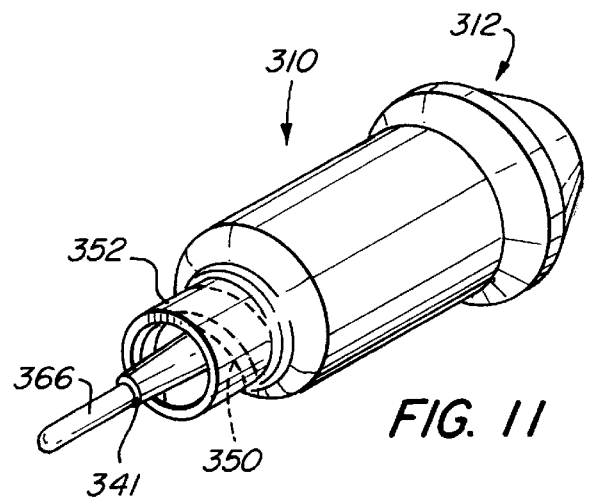
FIG. 11 is a perspective view illustrating another embodiment.

FIG. 9 and 10 illustrate another embodiment of the present invention. In this embodiment a twist-off tab forms a frangible seal or diaphragm which is associated with a reduced diameter end of a cartridge or capsule. Referring to FIG. 9, a body portion 210 is adapted to receive a material to be mixed. One end of the body portion 210 has a relatively large opening at one end to receive a plug or piston, not shown in FIG. 9. A longitudinal vent 215 is placed in the body portion 210. The vent 215 extends only partially along the length of the body portion 210. Near or adjacent the relatively large opening is a holding portion or collar 212. The holding portion 212 is adapted to be received by any conventional delivery system, such as a syringe. The other end of the body portion 210 has a reduced diameter end or portion 238. The reduced diameter end or portion 238 has a passage therein. The passage has a narrowed diameter portion 237 intermediate either end of the passage. On one end of the passage is a rear passage opening having an angled surface 239. On the other end of the passage is a front passage opening having an angled surface 235. Associated with the reduced diameter portion 238 is a tab 266. Tab 226 provides a frangible diaphragm or seal 240 to the passage formed by angled surfaces 239 and 235, and seals the passage in the reduced diameter portion 328. The thin walled section 241 permits the tab 226 to be twisted off, broken away, or removed from the reduced diameter portion 238 providing an opening to the passage formed by angled surfaces 239 and 235. An angled surface 234 is formed on the reduced diameter portion 238. At the rear portion of the angled surface 234 is an external shoulder 236.

FIG. 10 schematically illustrates the cartridge or capsule with the twist-off tab 226, illustrated in FIG. 9, removed and a delivery portion 216 attached. The delivery portion 216 is similar to the delivery portion illustrated in the prior figures, and is generally made of plastic with a bendable cannula 218 placed there through. The cannula 218 is preferably made of metal, but also may be made of plastic or other similar material. A rear portion of the cannula 218 is guided by the angled surface 235 through the passage formed thereby and communicates with or extends into the body portion 210. The narrowed diameter portion 237 holds and seals around the cannula 218. The delivery portion 216 is pushed or snap-fit onto the reduced diameter end or portion 238. Flange 228 helps in grasping the delivery portion 216. An internal shoulder 233 formed on the delivery portion mates with the external shoulder 236 formed on the reduced diameter end or portion 238 thereby effecting a snap-fit securely holding the delivery portion onto the body portion 210. A plug 214 is inserted into the relatively large rear opening of the body portion 210. The plug 220 has a plurality of flexible ears or handles 220 that assist in grasping and inserting the plug 214 into the body portion 210. The material 260 within the body portion 210 can be dispensed or extruded by advancing the piston or plug 214 with any conventional applicator, such as a syringe, not shown.

The operation of this embodiment is readily appreciated with reference to FIGS. 9 and 10. A material, preferably a dental material 260, is placed within the body portion 210. The tab 266 forms a frangible diaphragm or seal 240 associated with the reduced diameter end 238 preventing material from escaping from the body portion 210. A plug 214 is inserted into the relatively large opening adjacent the holding portion 212 and the material is mixed, if mixing is required. After mixing, tab 266 is removed. The rear end of cannula 218 in the delivery portion 216 is then placed in the passage formed by angled surfaces 239 and 235. The delivery portion is securely held onto the body portion 210 with the complementary or mating internal shoulder 233 and external shoulder 236. The cartridge is then placed in a dispenser or syringe and the material 260 may then be dispensed or extruded providing accurate and precise placement.

Figure 12:
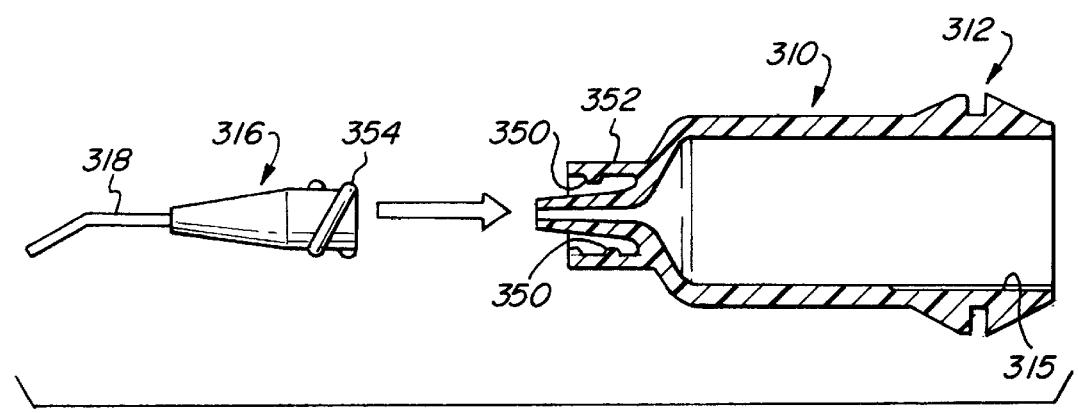
FIG. 12 is a partial cross section of the embodiment illustrated in FIG. 11.

FIG. 12 and 13 illustrate another embodiment of the present invention. The dental cartridge in this embodiment has a body 310 with a holding or collar portion 312 and an initially closed front portion. The front portion comprises a socket 352 having an internal thread 350 and a frangible nose or tab 366 forming a closed end. The nose or tab 366 has a reduced wall thickness intermediate either end. The nose or tab 366 can be either broken or cut off forming a frangible seal permitting the opening of the closed end. FIG. 12 illustrates the placement of a delivery portion 316 on the front end of the body 310 forming a complete dental cartridge. The delivery portion has a cannula 318 on one end and has a thread 354 on the other end configured to mate with the thread 350 formed within the socket 352. The body portion 310 may have a longitudinal vent 315 formed on the inside of the body portion 310 to facilitate the insertion of a plug, not shown.

FIGS. 13–16 illustrates another embodiment of the present invention. FIG. 13 illustrates the front end of a body portion 410. The front end has opposing hooks 428. The opposing hooks 428 have a inner shoulder 433. The opposing hooks 428 are formed around a reduced cylindrical portion 438. At the end of the reduced cylindrical portion 438 a tab 466 is formed initially closing or sealing the end.

Intermediate between the reduced cylindrical portion 438 and the tab 466 is a reduced wall thickness 441. The reduced wall thickness 441 permits easy removal of the tab 466 SO that the front end can be opened. FIG. 14 is a front end view that better illustrates the opposing hooks 428. FIG. 15 illustrates the placement of a delivery portion 316 on the front end of the body 410. The delivery portion 316 has a cannula 318 and threads. The delivery portion 316 is the same as the delivery portion illustrated in FIG. 12. FIG. 16 illustrates the placement of another type of delivery portion 416 on the front end of the body 410. The delivery portion 410 has an open nozzle 418 on one end and a flange 419 on the other end. The flange 419 is held by the opposing hooks 428. Accordingly, the front end of body 410 is adapted to hold a variety of different delivery portions 316 and 416.

Figure 17:
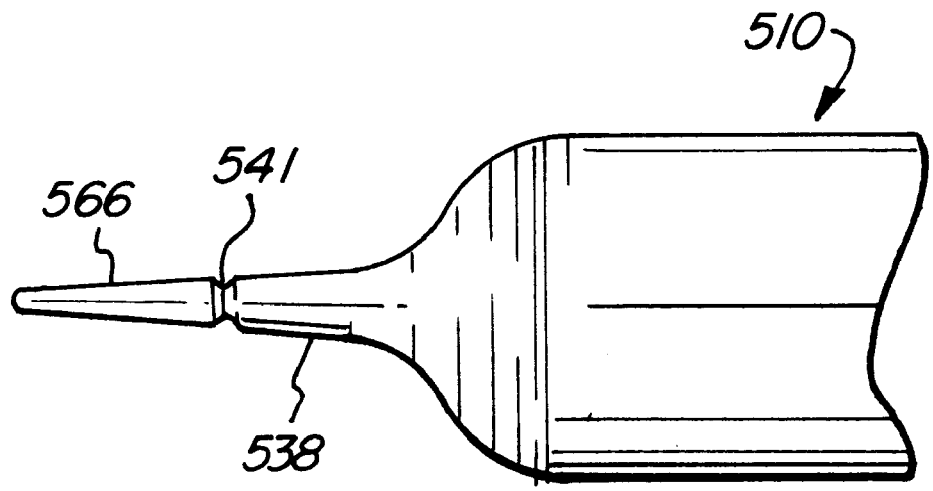
FIG. 17 is a partial side view illustrating the front portion of another embodiment of the present invention.
Figure 18:
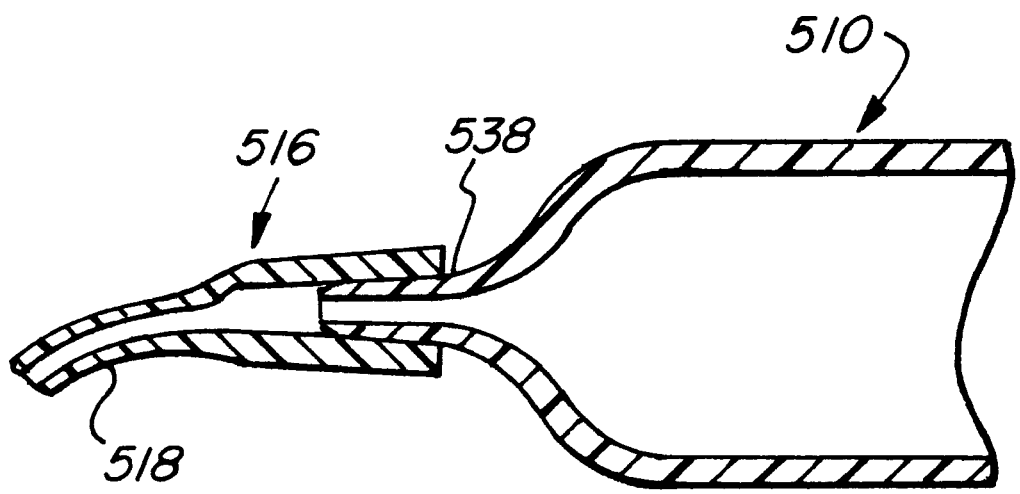
FIG. 18 is a partial cross section illustrating the embodiment illustrated in FIG. 17 with a delivery portion attached.

FIGS. 17 and 18 illustrates another embodiment of the present invention. In this embodiment a delivery portion 516 is held by friction onto the front end of body 510. Body 510 has a reduced cylindrical portion 538 with a closed nose or tab 566 having an intermediate reduced wall thickness 541. As illustrated in FIG. 18, after removal of the closed nose or tab 566 the delivery portion 516 is forced onto the reduced cylindrical portion 538 permitting dispensing of a dental material, not shown, from the nozzle 518.

Accordingly, it should be appreciated that the present invention, in providing a cartridge that has a snap on or pop on delivery portion or cap, clearly advances the art in delivering dental material. By permitting the dentist to control and vary the amount of liquid to be mixed with a powder, the volume of material may be increased over existing capsules. Additionally, the viscosity of the material may be easily adjusted by the dentist. The delivery portion or cap may come in a variety of different sized cannulas such that the dentist can choose a particular sized cannula having a particular diameter bore or lumen to be placed on a common cartridge body. This is particularly advantageous in that it permits the dentist to mix or prepare dental material to a desired viscosity or consistency for a particular application. Accordingly, the dentist need not compromise the desired viscosity for use in a particular application because of a limitation of available cannula sizes. The different delivery portions or caps may even be color coded to identify and distinguish the different diameter cannula sizes available. Additionally, different lengths of cannula may be used and selected by the dentist, depending upon application. Further, by providing a cannula extending into the interior space of the delivery portion or cap and using the cannula for rupturing the diaphragm, the rupturing of the diaphragm is assured. Therefore, the diaphragm may be made sufficiently strong so as to avoid any unintentional rupturing and spillage of the dental material prior to being prepared or mixed. The plug facilitates insertion and removal so that the dentist can conveniently prepare the dental material. Typically, a powder is initially placed within the cartridge body and the dental material is prepared by removing the cap or plug and inserting a liquid catalyst within the cartridge body. The cap or plug is then replaced during mixing. The cartridge body is placed into a mechanical mixer or amalgamator prior to placement of the delivery portion or cap thereon. The dentist is assured that the diaphragm or frangible seal will be sufficiently durable so as to avoid any unintentional rupturing of the frangible seal and inadvertent or unintentional dispensing of any material contained within the cartridge body. After mixing the dentist places the delivery portion or cap onto the reduced diameter end causing the frangible seal to rupture. In another embodiment, the dentist simple removes the twist-off tab and then places the delivery portion or cap onto the reduced diameter end. The dental material can then be conveniently dispensed. The cartridges or capsules may be sold empty or pre-filled with material. The cartridges may also be pre-filed with one component of material, such as a predetermined amount of powder, and a liquid second component that is placed in the cartridge by the dentist. Additionally, the frangible seal or diaphragm may be place anywhere along the passage formed in the reduced diameter end or portion as long as a temporary seal is provided. The frangible seal need only be associated with the reduced diameter portion or end. Additionally, it should be appreciated that while the present invention has particular applicability to dispensing of dental material, any type of material may be utilized with the present invention.

While several different embodiments of the present invention have been illustrated and described, it will be obvious to those skilled in the art to apply the teachings of the present invention. As a result, various modifications may be made without departing from the spirit and scope of this invention.

What is claimed is:

1. A dental cartridge kit comprising:

a cartridge having a body portion having an opening at one end and a reduced neck defining a passage at the other end thereof, a laterally outwardly extending collar circumscribing said opening at one end of said body portion, means for sealing said passage, said sealing means including a sealing cap integrally connected to said reduced neck at the discharge end of said passage, a laterally extending angled surface circumscribing said reduced neck at the discharge end of said passage, a frangible portion circumscribing said reduced neck adjacent said discharge end of said passage between said angled surface and said sealing cap to facilitate the severance of said sealing cap from said reduced neck, and a plurality of nozzle means for detachably connecting to said reduced neck upon the severance of said sealing cap, each of said plurality of nozzle means including a cap, a cannula connected to each of said caps, said caps having a latching ramp complementing said angled surface for interlocking said cap to said reduced neck, and a displaceable piston sealing the open end of said body portion, each of said plurality of caps having a different sized cannula, whereby a dentist may choose among said plurality of caps depending upon a preference of the dentist.

2. A dental cartridge kit as in claim 1 wherein:

each of said plurality of caps are a different color.

3. A dental cartridge kit as in claim 1 wherein:

said plurality of caps are sized base upon length of said cannula.

4. A dental cartridge kit as in claim 1 wherein:

said plurality of caps are sized base upon diameter of the lumen of said cannula.

5. A dental cartridge kit as in claim 1 wherein:

said canula is bendable.

6. A dental cartridge kit as in claim 5 wherein:

said canula is metal.

7. A dental cartridge kit as in claim 1 wherein:

said canula is plastic.

8. A dental cartridge for use in dispensing a dental material needing to be mixed comprising:
   a cartridge body made of plastic, said cartridge body having a longitudinal axis;
   a reduced diameter portion integrally formed on one end of said cartridge body, said reduced diameter portion having a front open end;
   a frangible seal formed within said reduced diameter portion separating the open end from said cartridge body, said frangible seal having a reduced thickness portion extending substantially entirely around its periphery except for a hinge portion, whereby the hinge portion effectively secures said frangible seal to said reduced diameter portion after said frangible seal is ruptured along the reduced thickness portion;
   a shoulder formed on said reduced diameter portion, a top surface of said shoulder having an inclined surface, said inclined surface sloping towards the open end at an angle to the longitudinal axis of said cartridge body, a first bearing surface being formed between the top surface and said reduced diameter portion, the first bearing surface being substantially perpendicular to the longitudinal axis of said cartridge body;
   a cap having an interior space adapted to fit over said reduced diameter portion, said cap having angled ramps extending into the interior space, the ramps having a second bearing surface adapted to mate with the first bearing surface on said shoulder;
   a metal cannula placed through said cap, one end of said metal cannula extending a predetermined distance into the interior space of said cap sufficiently far to rupture said frangible seal when said cap is placed on said reduced diameter portion and said first and second bearing surfaces are mated to each other;
   a rear open end formed in another end of said cartridge body;
   a collar adjacent said rear open end adapted to be received by an applicator;
   a plug adapted to fit within said rear open end; and
   flexible ears extending radially and placed on one end of said plug, whereby said flexible ears are easily grasped for removing said plug yet easily bend to fit within said rear open end of said cartridge body,
   whereby components of a dental material to be mixed can be sequentially placed within said cartridge body and mixed without unintentionally rupturing said frangible seal.

9. A dental cartridge for use in dispensing a dental material needing to be mixed comprising:
   a cartridge body made of plastic, said cartridge body having a longitudinal axis;
   a reduced diameter portion integrally formed on one of said cartridge body, said reduced diameter portion having a passage and a front end;
   a twist-off tab forming a frangible seal at the front end of the passage formed in the reduced diameter portion;
   a shoulder formed on said reduced diameter portion, a top surface of said shoulder having an inclined surface, said inclined surface sloping towards the open end at an angle to the longitudinal axis of said cartridge body, a first bearing surface being formed between the top surface and said reduced diameter portion, the first bearing surface being substantially perpendicular to the longitudinal axis of said cartridge body;
   a cap having an interior space adapted to fit over said reduced diameter portion, said cap having angled ramps extending into the interior space, the ramps having a second bearing surface adapted to mate with the first bearing surface on said shoulder;
   a metal cannula placed through said cap, one end of said metal cannula extending a predetermined distance into the interior space of said cap sufficiently far to enter the passage within said reduced diameter portion and said first and second bearing surfaces are mated to each other;
   a rear open end formed in another end of said cartridge body;
   a collar adjacent said rear open end adapted to be received by an applicator;
   a plug adapted to fit within said rear open end; and
   flexible ears extending radially and placed on one end of said plug, whereby said flexible ears are easily grasped for removing said plug yet easily bend to fit within said rear open end of said cartridge body,
   whereby components of a dental material to be mixed can be sequentially placed within said cartridge body and mixed without unintentionally rupturing said frangible seal.

10. A cartridge comprising:
    a body portion having an opening at one end and a reduced neck defining a passage at the other end thereof,
    a laterally outwardly extending collar circumscribing said opening at one end of said body portion,
    means for sealing said passage,
    said sealing means including a sealing cap integrally connected to said reduced neck at the discharge end of said passage,
    a laterally extending angled surface circumscribing said reduced neck at the discharge end of said passage,
    a frangible portion circumscribing said reduced neck adjacent said discharge end of said passage between said angled surface and said sealing cap to facilitate the severance of said sealing cap from said reduced neck,
    and a nozzle means detachably connected to said reduced neck upon the severance of said sealing cap,
    said nozzle means including cap,
    a cannula connected to said cap,
    said cap having a latching ramp complementing said angled surface for interlocking said cap to said reduced neck,
    and a displaceable piston sealing the open end of said body portion.

11. A method of mixing and dispensing a dental material comprising the steps
    of preloading a predetermined amount of a dental material into a dispensing cartridge which is sealed at its discharging end by a seal,
    forming said seal with a reduced frangible portion circumscribing a peripheral portion of said seal,
    sealing the filling end of the dispensing cartridge with a displaceable piston upon the filling thereof with said dental material,
    storing the cartridge containing said preloaded dental material until ready for use,
    removing the displaceable piston prior to using,
    placing a predetermined amount of a second dental material in said cartridge to be mixed with said first dental material whereby the dentist may selectively adjust the ratio of said first and second dental materials, replacing the displaceable piston to reseal the filling end of the cartridge, mixing the first and second dental materials in situ within said cartridge to form a homogeneous mixture of said first and second dental materials, fracturing said frangible seal, and effecting the displacement of said piston to extrude the homogeneous mixture of said first and second dental material directly where needed.

12. The method as defined in claim 11 wherein the preloading of the first mentioned dental material is a powder.

13. The method as defined in claim 11 wherein the placement of said second dental material is a liquid.

14. A method as in claim 11 wherein:

the placing of said first dental material is a powder; and the placing of said second dental material is a liquid.

15. A method as in claim 11 wherein the placing of:

said first dental material is a paste; and the placing of said second dental material is a liquid.

* * * * *